United States Patent [19]

Czinner

[11] Patent Number: 4,805,679
[45] Date of Patent: Feb. 21, 1989

[54] APPARATUS AND METHOD FOR PROCESSING LUMBER

[75] Inventor: Robert L. Czinner, Toronto, Canada

[73] Assignee: Integrated Wood Research Inc., Agincourt, Canada

[21] Appl. No.: 148,302

[22] Filed: Jan. 25, 1988

[51] Int. Cl.$^4$ .................... B27B 1/00; G01N 3/20
[52] U.S. Cl. .................... 144/357; 73/849; 83/364; 83/370; 144/2 R; 144/91; 144/363; 144/381
[58] Field of Search .............. 144/2 R, 3 R, 356, 357, 144/363, 381, 90 R, 91; 83/364, 365, 370, 371; 73/849

[56] References Cited

U.S. PATENT DOCUMENTS

| | | | |
|---|---|---|---|
| 4,164,248 | 8/1979 | Rysti | 144/356 |
| 4,207,472 | 6/1980 | Idelsohn et al. | 144/357 |
| 4,589,288 | 5/1986 | Porter et al. | 73/849 |

FOREIGN PATENT DOCUMENTS

| | | | |
|---|---|---|---|
| 536959 | 11/1976 | U.S.S.R. | 144/356 |
| 2043265 | 10/1980 | United Kingdom | 73/849 |

Primary Examiner—W. Donald Bray
Attorney, Agent, or Firm—Smart & Biggar

[57] ABSTRACT

This invention relates to a method and an apparatus for the cutting of dressed lumber to achieve the optimum valve of cut pieces based upon the specific structural and surface defect characteristics of each board, as well as upon historical demand, business inventory and market factors. The invention includes the use of a Modulous of Elasticity test and photo-electric surface scanners in order to determine these specific structural and surface defect characteristics.

30 Claims, 4 Drawing Sheets

APPARATUS AND METHOD FOR PROCESSING LUMBER

This invention relates to a method and an apparatus for the cutting of dressed lumber to achieve the optimum value of cut pieces based upon the specific structural and surface defect characteristics of each board of dressed lumber, as well as upon historical demand, business inventory, and market factors.

It is common practice to grade lumber using the human eye. This "visual" grading system attempts to determine the structural capabilities of a board by its apparent surface defects. The appearance of these defects thereby defines its grade. In Canada and the United States, visually graded lumber is classified into one of five distinct grades. Lumber which is to be used in structural applications must fall into one of the top three grades: namely, select structural; No. 1 grade; and, No. 2 grade.

This traditional grading method is not precise, however, as apparent defects are often not actual defects that affect the structural capabilities of the lumber. Moreover, there are some defects within the lumber that are not apparent to the human eye.

In visual grading, there are also inherent problems of human judgment. Thus, while the grading often results in lumber being graded less than its true grade, it can also result in lumber being graded better than its true grade. It is more common, however, for human graders using visual analysis to over-compensate for apparent defects and to undergrade the quality of the cut board. This discrepancy represents a significant cost to the lumber industry because the undergraded boards are sold for less money than their true value.

In the past, primary lumber sawmills have attempted to overcome these problems of human visual grading by using a photo-electric scanning apparatus that assists in assessing a few of the specific surface defect characteristics of lumber such as "wane" and "knots". This method has hitherto been used only with "rough", not dressed, lumber.

Generally, this method has involved moving, by conveyor, rough lumber pieces, which have just been cut, beneath an optical scanning system that measures the characteristics of light reflected from the lumber piece and translates these measurements as digitized signals, into a reading of the specific characteristics recognized from the surface of the lumber.

While photo-electric scanning permits faster, and generally more accurate, analysis than by human visual grading, it remains subject to the problem that it is limited to identifying only the surface characteristics of the lumber. As a result, this method similarly tends to undergrade the quality of the lumber.

In order to avoid the continued undergrading of lumber, it would be necessary to actually know how much weight, (ie. load) a board could carry before it would break. This, however, requires knowledge about the actual strength characteristics of the board along its entire length. The point at which a structural product, such as lumber, breaks is called its Modulous of Rupture (MOR).

A non-destructive test to determine the rupture point of a board has not yet been found. However, it is known that there is a direct proportionate relationship between a board's ability to bend and the point at which it will break. The force required to deflect a board a pre-determined amount is called its Modulous of Elasticity (MOE). The MOE can therefore be measured in a non-destructive manner.

Previously, the MOE test has only been used on visually graded finished pieces of lumber which have been determined to be structurally usable, so that the best, select pieces can be sorted out and sold at higher prices. In this application, only the average MOE for the entire board is considered.

The problem with the prior art, however, is that it does not provide a system that correlates "apparent" defects with a board's objective structural characteristics in order to achieve its most valuable use.

Moreover, the MOE has not yet been used as a tool to test a piece of lumber to determine the cut pattern which would result in its maximum market value. As a result, individual pieces of lumber are usually sold below their optimum value as there has not been a method of grading which is "tolerant" of defects.

By making the Modulous of Elasticity test on the lumber piece, the result of the Modulous of Elasticity test can be combined with the visual surface scan to reduce the likelihood of under-grading. The MOE test can be designed to provide digital output, and a computer can thus be programmed to control the cutting patterns of the lumber so as to achieve optimum quantity and value of the resultant pieces. Moreover, the computer can be programmed to find short pieces of a particular grade of lumber so as to there-by provide a high quantity of optimum graded lumber which can be jointed together without a loss of the structural characteristics. The concept of cutting lumber into high grade shortened pieces and joining the graded shortened pieces is of significant commercial value.

Because of the apparatus required to measure the MOE of a piece of lumber, it is not possible to determine the MOE at either end of the piece (ie. usually the last 6" of each end of the board). By measuring the MOE continuously along the measurable length of the lumber and by combining this information with the information from the visual surface scan, a highly accurate approximation of the MOE for these "unmeasurable" ends of the lumber can therefore be extrapolated.

It is an object of this invention to provide a method and apparatus that cuts finished lumber into pieces that yield dependable structural quality as well as optimum market value.

It is an object of the invention to make use of the Modulous of Elasticity test along the length of a piece of lumber with a view to achieve, by cutting, the most profitable yield of the resultant pieces.

It is also an object to make use of a measurement of visual characteristics of the surface of a piece of lumber in combination with the Modulous of Elasticity to achieve the most profitable yield of pieces, graded to objective standards. By combining the values of these two measurements, the yield of highest value cut lumber pieces is introduced.

It is a further object of the invention to provide a computerized grading method of lumber which is optimally tolerant of defects in the lumber.

According to one aspect of this invention, there is disclosed a method of cutting lumber pieces into an optimum number of pieces of optimum value comprising the steps of: measuring the modulous of elasticity along the length of a piece of lumber to determine its structural characteristics and capabilities; scanning the surface of the lumber piece for visual markings to determine possible structural defects; cutting the lumber piece into graded pieces as dictated by said measurements of modulous of elasticity and said surface scanning to achieve the optimum number of pieces of predetermined value.

According to another aspect of this invention, there is disclosed a method of cutting lumber pieces into an optimum number of pieces of optimum value comprising the steps of: measuring the modulous of elasticity of a pre-determined length of a piece of lumber at locations along the length of lumber to determine its structural characteristics; cutting said lumber piece into an optimum quantity of graded pieces as determined by said measurements of the modulous of elasticity and by analyzing the structural effect of defects discovered by scanning and stress rating.

According to another aspect of this invention, there is disclosed a method of cutting lumber pieces into an optimum number of pieces of optimum value comprising the steps of: moving a lumber piece along a conveyor means to a first station having a modulous of elasticity measuring means; at said first station, measuring the modulous of elasticity along the length of said lumber piece; sending the information gathered at said first station via a first transfer interface system to computer system; moving the lumber piece along a conveyor means from the first station to a second station having a surface scanning means; at the second station, scanning the lumber piece to determine its surface characteristics; sending the information gathered at said second station via a second transfer interface system to said computer system to which the information from the first station has been sent; comparing the information gathered by said modulous of elasticity measuring means and said surface scanning means in the computer system, and determining a cutting pattern for the lumber within the computer system; sending instructions via a third transfer interface system from the computer system to a third station having means for cutting the lumber; cutting the lumber into pieces of optimum grade value at said third station according to the instructions sent from the computer system.

According to another aspect of this invention, there is disclosed an apparatus for cutting lumber pieces into an optimum number of pieces of optimum value comprising: two preliminary stations, one of said two preliminary stations having a modulous of elasticity measuring means for measuring the modulous of elasticity between fixed points along the length of the lumber piece, the other of said preliminary stations having a surface scanning means for determining surface characteristics of the lumber piece; a conveyor means for moving the lumber piece to and from each of said preliminary stations; a computer system for receiving and comparing information gathered by the modulous of elasticity measuring means and the surface scanning means, said computer system being programmable to determine a cutting pattern of the lumber in response to the input of the information gathered by the modulous of elasticity measuring means and the surface scanning means; at least one further station having a cutting means to cut the lumber piece in a pattern determined by said computer system.

The invention will be readily understood after reading the following description given in conjunction with the drawings in which.

Figure 1:
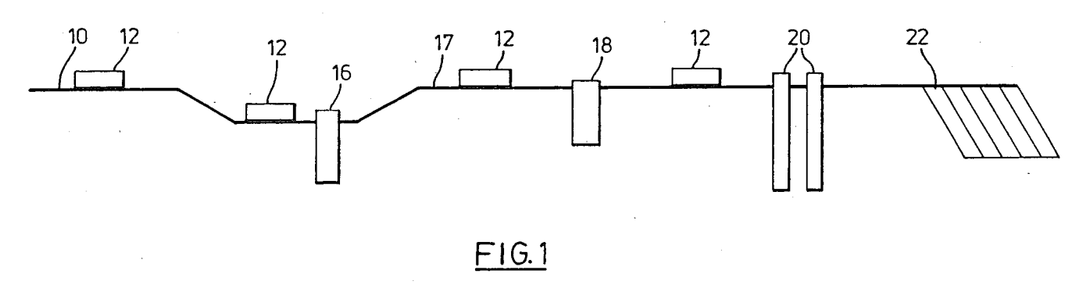
FIG. 1 is a schematic side elevation of an apparatus for practising the invention.
Figure 7:
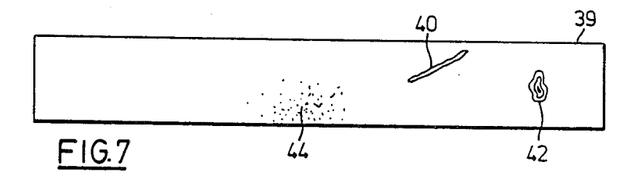
FIG. 7 shows the top surface of another piece of lumber of the type that can be cut with this invention; and, FIG. 8 shows the piece of lumber of FIG. 7 cut into the pieces directed by the computer system.

FIG. 1 is a schematic side elevation of an apparatus for practising the invention. This apparatus has a conveyor 10 for conveying monitored pieces of dressed lumber 12, similar to that shown in FIGS. 5 and 7, to a MOE measuring station 16, to a second conveyor 17, then to a surface scanning station 18, then to cutting stations 20, and then to a sorting and stacking area or station which is generally indicated by the numeral 22. Each piece of lumber 12 stops at the MOE measuring station 16, the surface scanning station 18 and the cutting stations 20, and then to a sorting and stacking area generally indicated by the numeral 22. At the MOE station 16 the modulous of elasticity of each board is measured when the conveyor stops at the station.

The MOE of a lumber piece, as determined between spaced apart points along its length, is an important characteristic of the lumber for grading purposes. The MOE is represented by the formula:

$$E = F*L^3/(4*D*W*H_3)$$

where:
 E=MOE, units can be expressed in millions of psi;
 F=applied force at the centre of the span, units can be expressed in pounds;
 L=length of span, units can be expressed in inches;
 D=displacement by force at the centre of the span, units can be expressed in inches;
 W=width of the lumber piece, units can be expressed in inches; and
 H=thickness of the lumber piece, units can be expressed in inches.

It has been found useful in determining an efficient cut pattern for a piece of lumber to measure E with an L of approximately 24 inches along the length of a piece of lumber. The length of the lumber piece in practise will be more often between 8 feet and 24 feet.

Height and width for a piece of lumber 12 will be substantially constant and usually in the order of 4–12" width and 1½" height, respectively.

In the test described herein, a force F is applied to achieve a constant deflection D of about 1/16" for a 1½" thick piece of lumber 12.

The variable is the applied force F and this variable is measured continuously along the length of the lumber as it is moved through the MOE measuring station 16. The resistance of the board to the applied force (ie. deflection) is measured and is fed into a computer system 24 to assist in determining the desired cutting pattern for the board, as will be described later.

Figure 4:
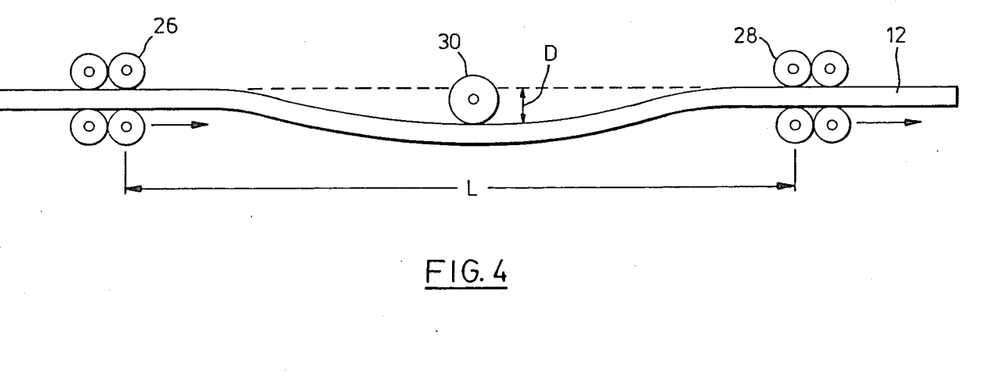
FIG. 4 is a schematic illustration of the testing apparatus at the MOE measuring station.

FIG. 4 is a schematic illustration of the testing apparatus at the MOE measuring station 16. The apparatus includes sets of clamping rollers generally indicated by the numerals 26 and 28. These rollers are designed to support the length of lumber between them and to move the lumber 12 along the conveyor.

As the lumber moves through the MOE measuring station 16, it is deflected a constant amount D by the roller 30. Depending on the MOE of the lumber between the rollers, the force F required to maintain the constant deflection will vary. This reading of resistance to this force is, as noted above, transmitted to the computer system 24 and is a useful characteristic in determining the optimum cut pattern for the lumber.

Measurements E are made continuously and the results are integrated over each inch of the lumber, or some other arbitrarily chosen length, for the purposes of computer system input.

The lumber 12, on leaving the MOE measuring station 16, is received by conveyor 17 and proceeds to the surface scanning station 18. The surface scanning station 18 scans a surface of the piece of lumber 12 for surface markings. This is achieved by transmitting light onto the top and edge surfaces and photo-electrically reading the reflected light to determine surface marking variations. For example, a black knot is relatively dark and will therefore generally absorb light. Accordingly, as little of the transmitted light is reflected, the photo-electric scanner would optically "read" or detect the presence of the knot.

The surface scanning means typically includes a set of cameras whose field of vision overlap with one another. Analog/digital processors are also provided for processing the information gathered by the cameras. A surface scanning means found to be suitable for this invention is the Dendro Maskin 4000, manufactured by Dendro Maskin.

In the Dendro Maskin 4000, each camera includes approximately 1,000 diodes. By controlling the lights when the picture is taken, each of the diodes in each camera will measure an exclusive area on the lumber piece of about 2×2 mm.

In use, the piece of lumber is positioned in front of the lens of the cameras. The piece of suitably lighted and a picture is taken of the whole exposed surface of the lumber piece. The process is synchronized by a master processor which is able to determine the location of blemishes, markings or knots on the lumber piece.

Figure 5:
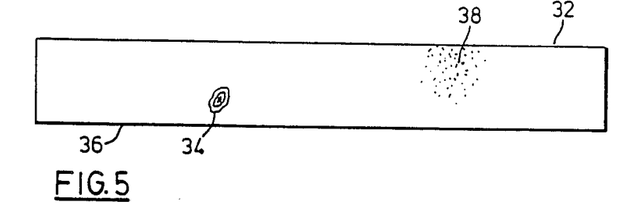
FIG. 5 shows the top surface, the worst face, of a piece of lumber of the type that can be cut with this invention.

FIG. 5 shows a typical lumber piece 32. Formed on the lumber piece 32 is a black knot 34 with a diameter of 5 cm, and its centre is located 190.5 cm from the back edge and 2.5 cm from the side edge 36. The black knot 34 would therefore likely fall within the confines of a grouping of nine of the 2×2 mm area sections.

The data sent to the computer system 24 from the surface scanning station would indicate that those nine 2×2 mm sections have a dark spot therein. The computer system 24 combines this information with the information obtained by the MOE reading station 16. Therefore, assuming that the MOE reading for the length of the lumber is low (ie. it takes a relatively small force to achieve the pre-determined constant deflection), the computer system 24 would confirm that the mark is more than a surface mark and is one that affects its structural strength. On the other hand, if the value of E remained high at the location of the apparent black knot, it would indicate that it is only a surface blemish that does not affect the structural strength of the lumber.

Looking at FIG. 5, a dotted area 38 indicates an area of decay in a typical piece of lumber. An area of decay would not necessarily be detected by the surface scanning station 18, but its weakening effect would should up on the data produced by the MOE measuring station 16. The length of the lumber piece for which there is decay would result in a computer output indicating removal of that section.

Having combined the information gathered by the MOE measuring station 16 and the surface scanning station 18, the computer system 24 operates the cutting stations 20 to cut the lumber into pieces of optimum value. In particular, the lumber may be cut horizontally (a "rip" pattern) or vertically (a "trim" pattern) and one cutting station 20 may be exclusively employed for trimming of lumber while the other cutting station 20 is employed for ripping. The cutting stations 20 can be of the standard design used in the trade to effect a trim and/or rip of the lumber in the usual manner, but in accordance with the computer output from the computer system 24.

The computer can be programmed to trim and rip according to any grading standard and to favour output of any particular grade and dimension combination according to current market value, and/or historical demand or open order requirements. The computer system 24 can also be programmed to cut the lumber into non-standard lengths as required and it can be programmed to send the cut lumber into these appropriate storage bins.

Figure 6:
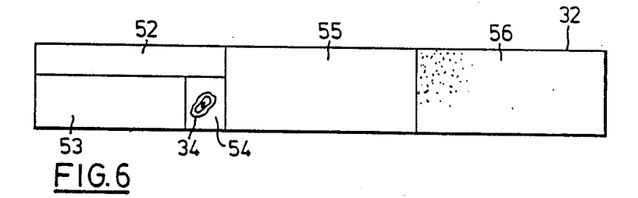
FIG. 6 shows the piece of lumber of FIG. 5 cut into the pieces directed by the computer system.
Figure 8:
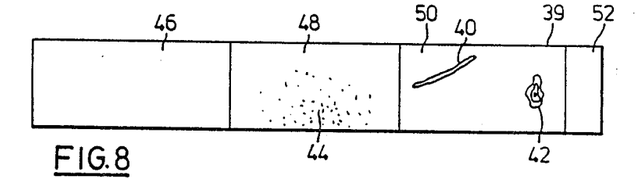

The piece of lumber shown in FIG. 5 could therefore be cut into pieces of lumber 52, 53, 54, 55 and 56, as shown in FIG. 6. Similarly, the lumber piece 39 shown in FIG. 7 having split 40, black knot 42 and decayed portions 44 could be cut into graded pieces 46, 48, 50 and 52, as shown in FIG. 8.

It is also significant that pieces of lumber may be joined by a finger jointing technique. By joining structurally sound shorter pieces, one can therefore get a greater yield of longer pieces of lumber of increased value.

Finger jointed lumber is widely used in Europe and in some parts of the United States. Finger jointed lumber has been found to meet, and for some applications surpass, the average strength criteria of non-jointed pieces of similar grade cut lumber.

Figure 3:
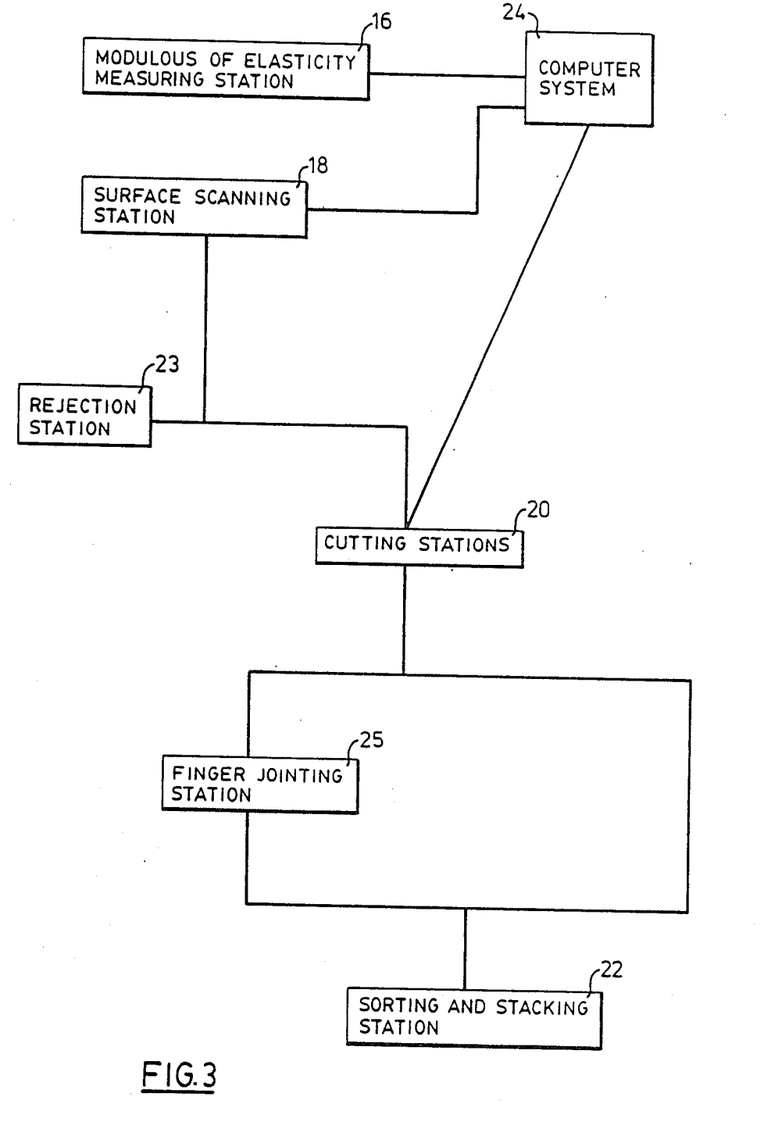
FIG. 3 is a schematic block diagram of an apparatus for practicing the invention.

This sytem can locate short lengths of cut lumber and direct them for wood fibre recovery by finger jointing. For example, although eight feet is commonly a standard length of cut lumber, there may not be very many eight foot lengths of grade A lumber pieces recoverable from the lumber being used. However, there would, of course, be a greater number of shorter lengths of grade A lumber available. This system can therefore request Grade A lumber which is as short as 6" in length, locate and cut them, and then recover them for finger jointing. A finger jointing station is indicated by the numeral 25 in FIG. 3, and is coordinated by the computer system 24.

Figure 2:
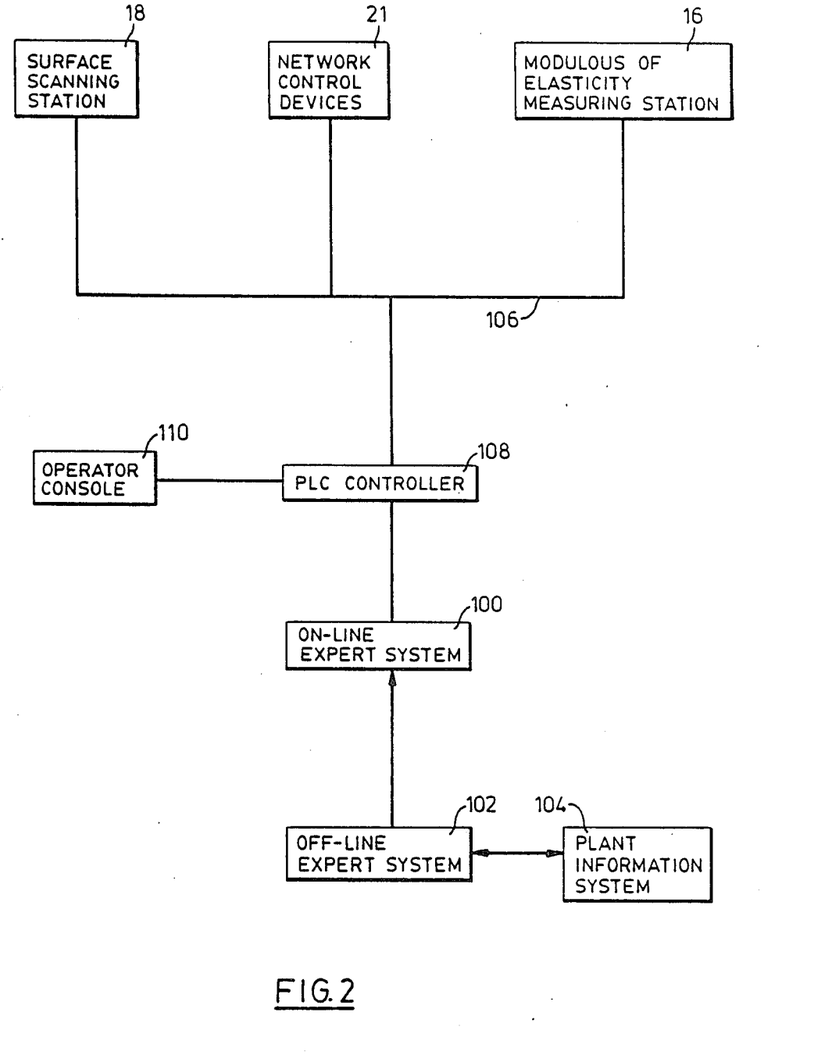
FIG. 2 is a schematic block diagram showing the computer interface system of an apparatus for practising the invention.

An overview of the computer system 24 is illustrated in FIG. 2 which is a schematic diagram of the system's interfaced network. There are three major information transfers in the network.

The first transfer of information is carried out when the off-line expert system 102 interacts with both the on-line expert system 100 and the plant's information system 104. The on-line expert system is a combination of computer hardware and software while the plant's information system 104 includes a listing of open orders, prices of the different grades of wood, historical production information, and inventory. The off-line expert system 102 accesses the information in the plant's information system 104 and is able to, on the basis of programmed parameters, assign an priority as to what sizes and grades of wood are the most desirable to cut. The off-line expert system 102 feeds the on-line expert system 100 the priority information on a periodic basis, for example once every shift.

The second transfer of information is carried out when the MOE measuring means and the surface scanning station 18 each analyze thelumber piece and send the data via the communication transfer interface 106 and the Programmable Logic Controller ("PLC") 108 to the on-line expert system 100.

The third transfer of information is carried out when the on-line expert system 100 matches the information sent to it from the off-line expert system 102 with the information sent to it from both the MOE measuring means and the surface scanning station 18, in order to determine an optimum trim and/or rip pattern. Moreover, the off-line expert system plays an important role in the manufacturing process as it not only determines what lumber storage bins are available, but it also determines what lengths of lumber should be cut to accommodate those storage bins. As well, the off-line expert system responds to the programmed parameters and to historical demand, business inventory, open orders and market factors so as to pre-determine the amount of raw lumber required for cutting the optimum number of pieces of lumber of optimum value. As a result, the computer system 24 is not only able to assign a priority as to what sizes and grades of lumber are most desirable, but it also ensures that the desired volumes, sizes and grades of lumber can practically and properly be handled and stored. The cutting stations 20 can then respond accordingly to the digital instructions forwarded by the on-line expert system.

The computer system 24 identifies this cutting plan to a human quality control operator who can choose either to accept or to reject this plan. The computer then instructs the cutting stations 20 via the Programmable Logic Controller ("PLC") 108 to execute its choice.

The PLC controller is the apparatus by which the on-line expert system 100 controls computer-controlled apparatus. The PLC controllers are dedicated to controlling external events, as instructed, and to relaying information back to the on-line expert system 100.

The computer-controlled ("CC") devices receive data from the PLC Controller 108 and act on that data and/or transmit to the PLC Controller after an apparatus event. For example, the speed at which the conveyor system runs, as instructed by the on-line expert system via the PLC Controller 108, would be sent through CC devices. Similarly, the cutting mecahnisms would be controlled via CC devices.

The PLC Cntroller 108 is interfaced to the MOE measuring station 16, the surface scanning station 18 and the other networked CC devices 21. The interface ensures that the instructions are properly transferred from the PLC Controller 108 to its correct destination.

An operator console 110 provides an override function and a reset function. Over-ride is required when the system jams or is unduly slowed down because of an overly defective piece of lumber that cannot be processed by the apparatus. The operator can override the computer system by rejecting the lumber piece via the rejection station 23. The reset function of the operator console is used to correct system confusion, which might result from a misaligned, or jammed, piece of lumber.

The foregoing is an example system and it is not intended that the scope of protection be limited to the single embodiment illustrated by extent to the invention as a whole as claimed in the appended claims.

I claim:

1. A method of cutting lumber pieces into an optimum number of pieces of optimum value comprising the steps of:
   measuring the modulous of elasticity along the length of a piece of lumber to determine its structural characteristics and capabilities;
   scanning the surface of the lumber piece for visual markings to determine possible structural defects;
   cutting the lumber piece into graded pieces as dictated by said measurements of modulous of elasticity and said surface scanning to achieve the optimum number of pieces of pre-determined value.

2. A method of cutting lumber pieces as claimed in claim 1, in which said modulous of elasticity is measured at locations along the length of said lumber piece by maintaining a constant deflection of said lumber piece between the ends of a pre-determined portion of said lumber piece and determining the magnitude of force required to maintain the deflection.

3. A method of cutting lumber pieces as claimed in claim 1, in which resulting pieces of cut lumber of like grade are jointed together.

4. A method of cutting lumber pieces as claimed in claims 1, 2 or 3 in which the modulous of elasticity is continuously measured along the length of said lumber piece and is used in conjunction with market value factors to determine the cutting pattern for the piece of lumber.

5. A method of cutting lumber pieces as claimed in claims 1, 2, or 3, in which the modulous of elasticity is measured continuously along the length of said lumber piece, and in which said cutting is done to achieve the optimum quantity of graded pieces of lumber of dependable structural strength without regard to the length of the individual pieces of lumber.

6. A method of cutting lumber pieces into an optimum number of pieces of optimum value comprising the steps of:
   measuring the modulous of elasticity of a pre-determined length of a piece of lumber at locations along the length of lumber to determine its structural characteristics;
   cutting said lumber piece into an optimum quantity of graded pieces as determined by said measurements of the modulous of elasticity and by analyzing the structural effect of defects discovered by scanning and stress rating.

7. A method of cutting lumber pieces as claimed in claim 6, in which said modulous of elasticity is measured at locations along the length of said lumber piece by maintaining a constant deflection of said lumber piece between the ends of a pre-determined portion of said piece of lumber and reading the magnitude of the force required to maintain the deflection.

8. A method of cutting lumber pieces as claimed in claim 6, in which lumber pieces of like grades are jointed together.

9. A method of cutting lumber pieces as claimed in claims 6, 7 or 8, in which the modulous of elasticity is continuously measured along the length of said lumber piece.

10. A method of cutting lumber pieces as claimed in claims 6, 7 or 8, in which the modulous of elasticity is continuously measured along the length of said lumber piece and in which said lumber piece is cut to achieve optimum quantities of graded pieces of lumber of dependable structural strength without regard to individual length.

11. A method of cutting lumber pieces into an optimum number of pieces of optimum value comprising the steps of:
   moving a lumber piece along a conveyor means to a first station having a modulous of elasticity measuring means;
   at said first station, measuring the modulous of elasticity along the length of said lumber piece;
   sending the information gathered at said first station via a first transfer interface system to computer system;
   moving the lumber piece along a conveyor means from the first station to a second station having a surface scanning means;
   at the second station, scanning the lumber piece to determine its surface characteristics;
   sending the information gathered at said second station via a second transfer interface system to said computer system to which the information from the first station has been sent;
   comparing the information gathered by said modulous of elasticity measuring means and said surface scanning means in the computer system, and determining a cutting pattern for the lumber within the computer system;
   sending instructions via a third transfer interface system from the computer system to a third station having means for cutting the lumber;
   cutting the lumber into pieces of optimum grade value at said third station according to the instructions sent from the computer system.

12. An apparatus for cutting lumber pieces into an optimum number of pieces of optimum value comprising:
   two preliminary stations, one of said two preliminary stations having a modulous of elasticity measuring means for measuring the modulous of elasticity between fixed points along the length of the lumber piece, the other of said preliminary stations having a surface scanning means for determining surface characteristics of the lumber piece;
   a conveyor means for moving the lumber piece to and from each of said preliminary stations;
   a computer system for receiving and comparing information gathered by the modulous of elasticity measuring means and the surface scanning means, said computer system being programmable to determine a cutting pattern of the lumber in response to the input of the information gathered by the modulous of elasticity measuring means and the surface scanning means;
   at least one further station having a cutting means to cut the lumber piece in a pattern determined by said computer system.

13. An apparatus for cutting lumber pieces as claimed in claim 12, wherein said modulous of elasticity measuring means includes a plurality of rollers in order to deflect the lumber piece between two points along the length of the lumber piece.

14. An apparatus for cutting lumber pieces as claimed in claim 12, further comprising an operator console for either resetting the apparatus when it jams or for removing an undesirable lumber piece from the apparatus.

15. An apparatus for cutting lumber pieces as claimed in claims 12, 13 or 14, further comprising a finger jointing station for joining two cut lumber pieces.

16. A method of cutting lumber pieces into an optimum number of pieces of optimum value as determined by the selection of specific dimensions of the output lumber pieces, in accordance with the number of storage bins available comprising the steps of:
   pre-determining the amount of lumber required to be cut into the optimum number of pieces of cut lumber of optimum value;
   measuring the modulous of elasticity along the length of each piece of lumber to determine its structural characteristics and capabilities;
   scanning the surface of each lumber piece for visual markings to determine possible structural defects;
   cutting each lumber piece into graded pieces as dictated by said measurements of modulous of elasticity and said surface scanning.

17. A method of cutting lumber pieces as claimed in claim 16, in which said modulous of elasticity is measured at locations along the length of each lumber piece by maintaining a constant deflection of said lumber piece between the ends of a pre-determined portion of said lumber piece and determining the magnitude of force required to maintain the deflection.

18. A method of cutting lumber pieces as claimed in claim 16, in which resulting pieces of cut lumber of like grade are jointed together.

19. A method of cutting lumber pieces as claimed in claims 16, 17 or 18 in which the modulous of elasticity is continuously measured along the length of each lumber piece and is used in conjunction with market value factors to determine the cutting pattern for the piece of lumber.

20. A method of cutting lumber pieces as claimed in claims 16, 17 or 18, in which the modulous of elasticity is measured continuously along the length of each lumber piece, and in which said cutting is done to achieve the optimum quantity of graded pieces of lumber of dependable structural strength without regard to the length of the individual pieces of lumber.

21. A method of cutting lumber pieces into an optimum number of pieces of optimum value comprising the steps of:
   pre-determining the amount of lumber required to be cut into the optimum number of pieces of cut lumber of optimum value;
   measuring the modulous of elasticity of a pre-determined length of each piece of lumber at locations along the length of lumber to determine its structural characteristics;
   cutting each lumber piece into an optimum quantity of graded pieces as determined by said measurements of the modulous of elasticity and by analyzing the structural effect of defects discovered by scanning and stress rating.

22. A method of cutting lumber pieces as claimed in claim 21, in which said modullus of elasticity is measured at locations along the length of each lumber piece by maintaining a constant deflection of said lumber piece between the ends of a pre-determined portion of said piece of lumber and reading the magnitude of the force required to maintain the deflection.

23. A method of cutting lumber pieces as claimed in claim 21, in which lumber pieces of like grades are jointed together.

24. A method of cutting lumber pieces as claimed in claims 21, 22 or 23, in which the modulous of elasticity is continuously measured along the length of each lumber piece.

25. A method of cutting lumber pieces as claimed in claims 21, 22 or 23, in which the modulous of elasticity is continuously measured along the length of each lumber piece and in which said lumber piece is cut to achieve optimum quantities of graded pieces of lumber of dependable structural strength without regard to individual length.

26. A method of cutting lumber pieces into an optimum number of pieces of optimum value comprising the steps of:
- pre-determining the amount of lumber required to be cut into the optimum number of pieces of cut lumber of optimum value;
- moving each lumber piece along a conveyor means to a first station having a modulous of elasticity measuring means;
- at said first station, measuring the modulous of elasticity along the length of each lumber piece;
- sending the information gathered at said first station via a first transfer interface system to computer system;
- moving the lumber piece along a conveyor means from the first station to a second station having a surface scanning means;
- at the second station, scanning the lumber piece to determine its surface characteristics;
- sending the information gathered at said second station via a second transfer interface system to said computer system to which the information from the first station has been sent;
- comparing the information gathered by said modulous of elasticity measuring means and said surface scanning means in the computer system, and determining a cutting pattern for the lumber within the computer system;
- sending instructions via a third transfer interface system from the computer system to a third station having means for cutting the lumber;
- cutting the lumber into pieces of optimum grade value at said third station according to the instructions sent from the computer system.

27. An apparatus for cutting lumber pieces into an optimum number of pieces of optimum value comprising:
- means for pre-determining the amount of lumber required to be cut into the optimum number of pieces of cut lumber of optimum value;
- two preliminary stations, one of said two preliminary stations having a modulous of elasticity measuring means for measuring the modulous of elasticity between fixed points along the length of the lumber piece, the other of said preliminary stations having a surface scanning means for determining surface characteristics of the lumber piece;
- a conveyor means for moving the lumber piece to and from each of said preliminary stations;
- a computer system for receiving and comparing information gathered by the modulous of elasticity measuring means and the surface scanning means, said computer system being programmable to determine a cutting pattern of the lumber in response to the input of the information gathered by the modulous of elasticity measuring means and the surface scanning means;
- at least one further station having a cutting means to cut the lumber piece in a pattern determined by said computer system.

28. An apparatus for cutting lumber pieces as claimed in claim 27, wherein said modulous of elasticity mesuring means includes a plurality of rollers in order to deflect the lumber piece between two points along the length of the lumber piece.

29. An apparatus for cutting lumber pieces as claimed in claim 27, further comprising an operator console for either resetting the apparatus when it jams or for removing an undesirable lumber piece from the apparatus.

30. An apparatus for cutting lumber pieces as claimed in claims 27, 28 or 29, further comprising a finger jointing station for joining two cut lumber pieces.

* * * * *